United States Patent
Nap et al.

[11] Patent Number: 5,971,955
[45] Date of Patent: Oct. 26, 1999

[54] DOUBLE BALLOON CATHETER WITH ULTRASONIC PROBE

[75] Inventors: Cornelis Philipus Nap, Zevenhuizen; Wilhelmus Petrus Martinus Maria van Erp, Leek, both of Netherlands

[73] Assignee: Cordis Corporation, Miami, Fla.

[21] Appl. No.: 08/963,742

[22] Filed: Nov. 4, 1997

Related U.S. Application Data

[63] Continuation of application No. 08/667,534, Jun. 21, 1996, abandoned.

[51] Int. Cl.⁶ .................................................. A61M 29/00
[52] U.S. Cl. ...................................... 604/101; 128/662.06
[58] Field of Search ............................... 606/1, 191–195; 604/96, 101; 128/662.06, 660.03

[56] References Cited

U.S. PATENT DOCUMENTS

| | | |
|---|---|---|
| 5,022,399 | 6/1991 | Biegeleisen . |
| 5,226,889 | 7/1993 | Sheiban . |
| 5,395,311 | 3/1995 | Andrews .................................. 606/159 |
| 5,423,838 | 6/1995 | Willard .................................... 606/159 |
| 5,429,136 | 7/1995 | Milo et al. .............................. 606/159 |
| 5,582,178 | 12/1996 | Yock ................................... 128/660.03 |
| 5,588,961 | 12/1996 | Leone et al. .............................. 604/96 |

FOREIGN PATENT DOCUMENTS

| | | |
|---|---|---|
| 0 441 384 A2 | 2/1990 | European Pat. Off. . |
| 36 39 321 A1 | 12/1985 | Germany . |
| WO 91/04708 | 4/1991 | WIPO . |

Primary Examiner—Michael Buiz
Assistant Examiner—William Lewis
Attorney, Agent, or Firm—Paul A. Coletti

[57] ABSTRACT

The invention relates to a catheter comprising a tube-like basic body with a distal end and a proximal end and at least two balloon members received at the distal end at a certain distance from each other, wherein an ultrasonic probe has been received between the balloon members. The ultrasonic probe comprises a series of piezo crystals and at least one multiplexer which can activate the piezo crystals in a phased manner.

6 Claims, 4 Drawing Sheets

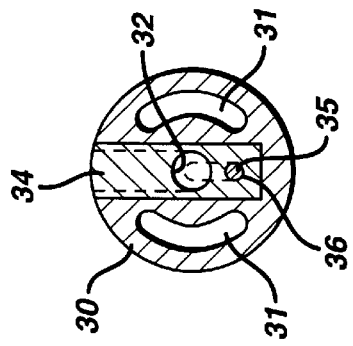
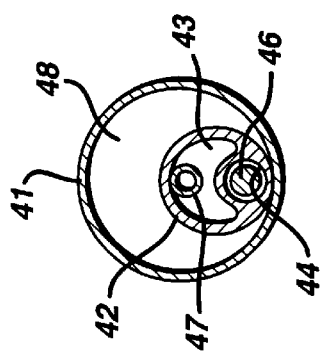
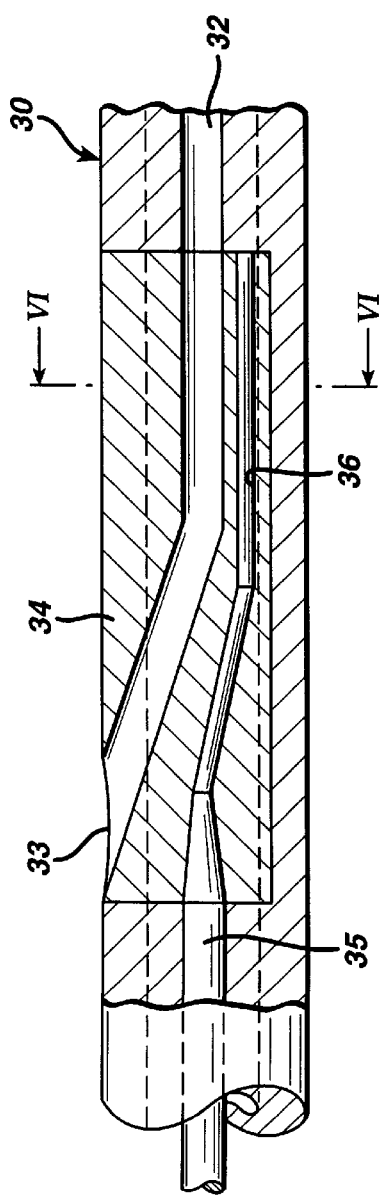
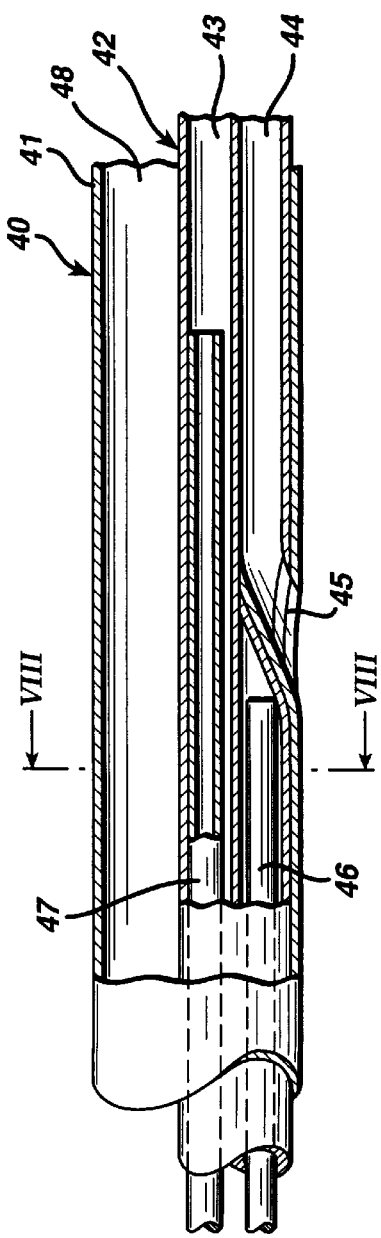

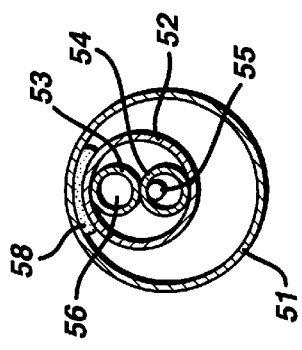
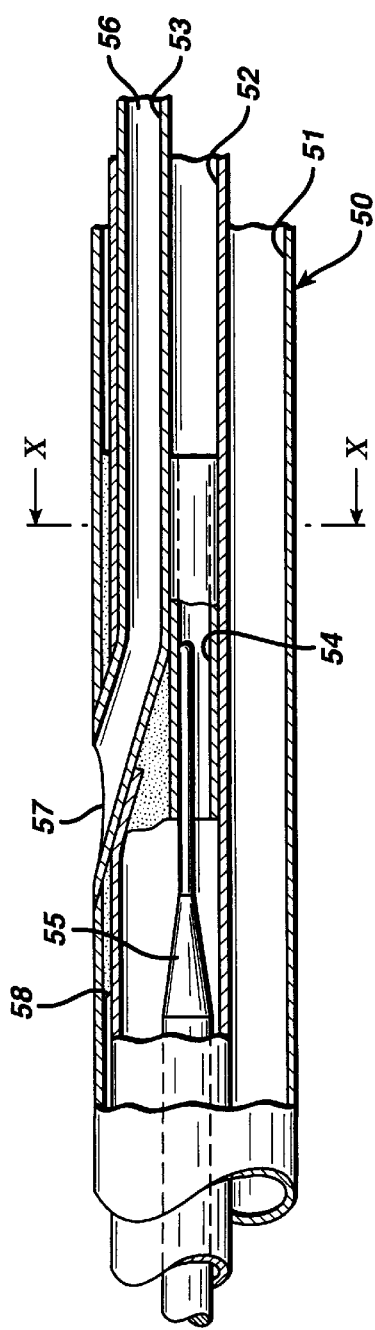

DOUBLE BALLOON CATHETER WITH ULTRASONIC PROBE

This is a continuation of application Ser. No. 08/667,534, filed Jun. 21, 1996, now abandoned.

FIELD OF THE INVENTION

The invention relates to a catheter designed to treat a narrowing in a body vessel of a patient, in particular a narrowing in a blood vessel.

BACKGROUND OF THE INVENTION

With such treatment it may be necessary to use three separate catheters. With a first catheter, provided with a dilatation balloon, the narrowing (or stenosis) is dilated. With a second catheter a stent is subsequently positioned at the site of the narrowing. This is done by positioning a stent in compressed state, placed around the balloon member of a catheter intended for that purpose in the area of the narrowing, inflating the balloon as a result of which the stent will expand, and generally, plastically deform, and subsequently deflating and withdrawing the balloon. A third catheter comprises an ultrasonic probe, and is used to generate an image of the narrowing or of the stent in situ by recording the transmitted ultrasonic waves on a suitable receiver and converting them into an image.

SUMMARY OF THE INVENTION

The object of the invention is to provide a catheter with which such treatment can be carried out more quickly and in a manner less burdensome to the patient.

This aim is achieved with a catheter as characterized herein. The first balloon of the catheter according to the invention can be a dilatation balloon. The second balloon may also be a dilatation balloon with a larger effective diameter or, in a suitable manner, a balloon used for the purpose of positioning a stent. With such an invention, the dilation, positioning the stent and ultrasonic imaging may be carried out using one and the same catheter. An additional advantage of the catheter according to the invention is that the latter can be considerably cheaper than the total costs of the three separate catheters.

Fluids under pressure are used to expand the balloon members, and are supplied via a separate interspace in between the tube-like bodies of the catheter.

Because the opening of the guide wire lumen in the outer wall of the basic body of the catheter is at the proximal side of the relatively proximal balloon member, it does not have to be fed onto the guide wire over its entire length, as a result of which the treatment can be carried out more easily and quickly.

The stiffening wire prevents the basic body of the catheter from buckling near the opening of the guide wire lumen.

DESCRIPTION OF THE DRAWINGS

The invention will be explained in greater detail in the following description with reference to embodiments illustrated in the accompanying figures, wherein:

FIG. 5 shows a longitudinal cross-section of yet another embodiment of the catheter according to the invention at the opening of the guide wire channel;

FIG. 6 shows a cross-section along the line VI—VI of FIG. 5;

FIG. 7 shows a cross-section of another embodiment corresponding to FIG. 5;

FIG. 8 shows a cross-section along the line VIII—VIII of FIG. 7;

FIG. 9 illustrates once again a longitudinal cross-section of another embodiment corresponding to FIG. 5; and FIG. 10 shows a cross-section along the line X—X of FIG. 9.

DETAILED DESCRIPTION OF THE INVENTION

Figure 1:
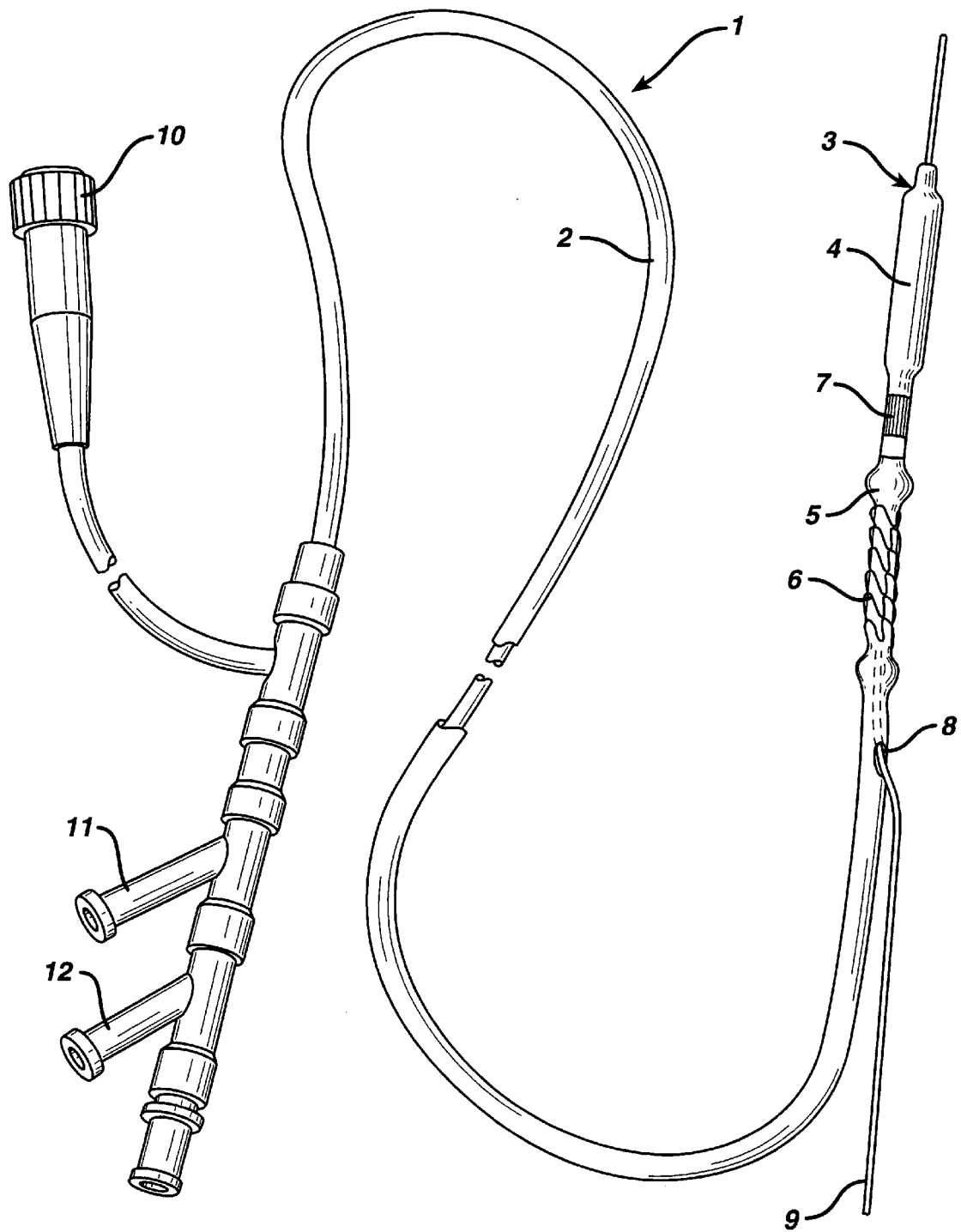
FIG. 1 shows a partly broken away perspective view of a catheter according to an embodiment of the invention.

The catheter 1 according to the invention as illustrated in FIG. 1 comprises a basic body 2 with a distal end 3. At the distal end 3 the catheter 1 is provided with a first balloon member 4, and at a certain distance thereof a second balloon member 5. The first balloon member 4 is intended to be used for dilatation treatment, whereas the second balloon 5 is to be used to position a stent 6. This stent 6 is introduced in compressed state placed around the balloon 5, is expanded at the required site by inflating the balloon 5 and left behind inside the body of the patient.

An ultrasonic probe 7 has been arranged in between the dilatation balloon 4 and the sent-positioning-balloon 5. Following dilatation with the balloon member 4 and positioning of the stent 6, the ultrasonic probe 7 is activated to generate an image on the imaging device of the area in which the stent has been positioned, in order to check that the treatment has been carried out properly.

In a manner to be described below in greater detail, a guide wire lumen has been arranged in the distal end 3 of the catheter 1, the opening 8 of which is situated at the proximal end of the second balloon member 5. A guide wire 9 can extend through the guide wire lumen and the distal end 3 of the catheter 1 can be advanced over this guide wire 9 to the stenosis to be treated.

At the proximal end of the catheter 1 a number of connecting members have been arranged which correspond with the three treatment members at the distal end of the catheter. The connector 10 is connected with the ultrasonic probe 7 via excitation conductors in a manner to be described in greater detail below. The connection 11 is connected via a lumen in the basic body 2 with the balloon member 4 in order to be able to supply to and remove from it fluid under pressure. In a similar manner the connection 12 is connected with the inside of the balloon member 5.

Figure 2:
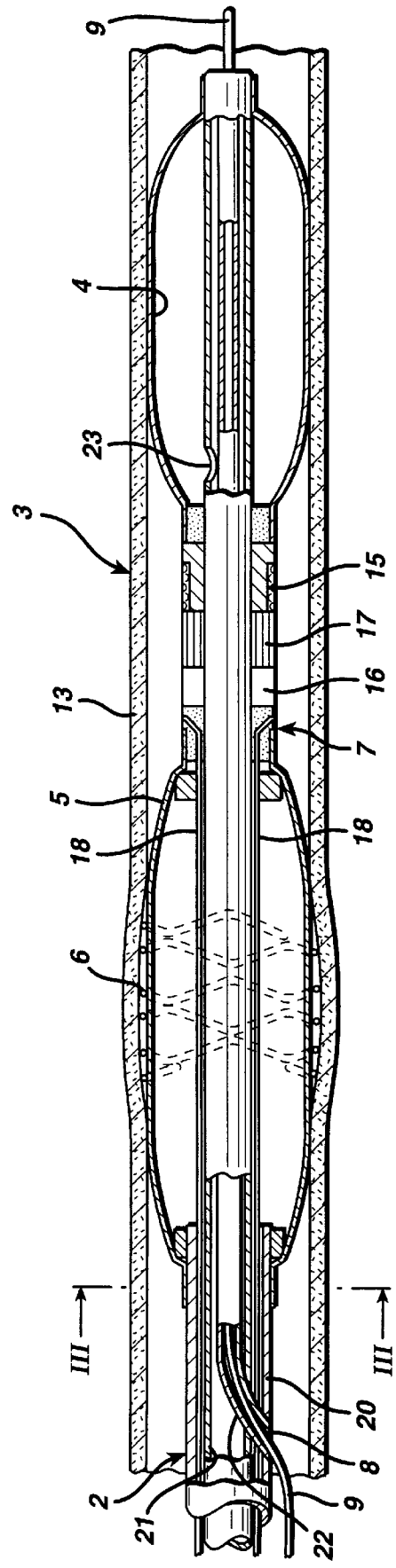
FIG. 2 shows the distal end-section of the catheter of FIG. 1 in a longitudinal cross-section.
Figure 3:
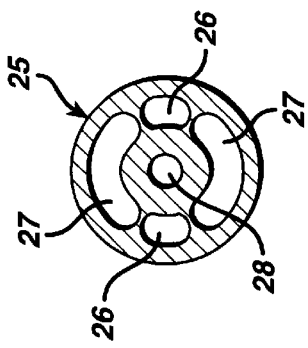
FIG. 3 shows a cross-section along the line III—III of FIG. 2.

FIG. 2 illustrates the distal end 3 of the catheter 1 in greater detail. It can be seen that the ultrasonic probe 7 has been arranged in between the balloon member 4 and the balloon member 5 placed at a certain distance thereof. In the case of this embodiment the ultrasonic probe 7 comprises a series of piezo crystals 15 which are connected via connectors 17 to one or more multiplexers 16. This multiplexer is activated via conductors 18 which are connected with the connector 10. The multiplexer 16 has been made in such a way that it can activate the piezo crystals 15 in a phased manner. As a result ultrasonic vibrations are generated which can be used to provide an image of the surroundings of this ultrasonic generator 7 in a manner known as such.

With an embodiment not illustrated here, the piezo crystals, the one or more multiplexers and the conducting wires may be mounted on a flexible sheet with a printed circuit. This sheet is folded round the basic body. In this way a very compact construction may be obtained.

The space in between the piezo crystal is filled with sound-insulating material.

As can be seen in FIG. 2, the basic body 2 of the catheter is made up of three coaxial tube-like members. The inner tube-like member 22 defines the guide wire lumen and receives the guide wire 9 during treatment. As described above, the opening of the guide wire lumen is preferably situated at the relatively proximal end of the relatively proximal balloon member 5 in the outer wall of the basic body 2. Suitable embodiments will be explained in greater detail with reference to the FIGS. 5–10.

The central tube-like body 21 extends to the distal tip of the catheter. Near the distal balloon member 4 an opening 23 has been formed int he wall of the central tube-like body. Via the interspace in between the inner tube-like body 22 and the central tube-like body 21, fluid under pressure can be supplied to the balloon member 4 through the opening 23.

In the same way the inside of the balloon member 5 is connected via the interspace in between the outer tube-like body 20 and the central tube-like body 21 with the proximal end in order to supply from there fluid under pressure for the purpose of inflating the balloon member 5.

Via the same interspace the conductors 18 extend to the proximal end, where they are connected to the connector 10.

Figure 4:
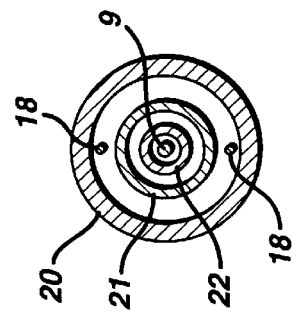
FIG. 4 illustrates the cross-section of another embodiment of the catheter according to the invention corresponding to FIG. 3.

The catheter according to the invention does not necessarily need to be made so as to have a basic body comprising a number of coaxial tube-like members. It is also possible to make the basic body in such a way that it constitutes one body comprising a number of lumens. Such an embodiment has been illustrated in FIG. 4.

The basic body 25 comprises a number of lumens 26, 27 and 28. The lumens 26 are for instance used to supply fluid under pressure to the relatively distal balloon which is used for dilatation treatment. The lumens 27 can be connected with the stent-positioning-balloon, and the central lumen 28 may be used as guide wire lumen.

It is obviously also possible to assemble the basic body in a different way. Another possibility is for example a tube-like body with two lumens, which has been received in an outer tube-like body comprising one lumen.

With the embodiment of the FIGS. 5 and 6, the basic body 30 also consists of one body comprising a number of lumens. The lumens 31 are intended to be used to convey fluid under pressure to the balloon members, whereas the lumen 32 in the distal section of the catheter serves as guide wire lumen. As can be seen in FIG. 5, an inserted piece 34 has been arranged at the proximal end of the relatively proximal balloon in the basic body 30, inside of which the central channel 32 has been led towards the lateral wall to form the opening 33.

In line with the channel 32, on the left-hand side as seen in FIG. 5, a stiffening wire 35 has been received of which the diameter decreases, and which extends into a specially formed channel 36 inside the insert 34. The stiffening wire 35 prevents buckling of the basic body 30 at the opening 33.

The basic body 40 of the catheter as illustrated in the FIGS. 7 and 8 is made up of a tube-like body 41, inside of which a tube-like body 42, comprising two lumens, has been received. The tube-like body 42 comprises a first lumen 43 and a second lumen 44. The lumen 43 is connected with the dilatation balloon, and the interspace 48, in between the outer tube-like body 41 and the inner tube-like body 42 received therein, is connected with the stent-positioning-balloon.

The second lumen 44 in the inner tube-like body 42 is the guide wire lumen, and has an opening 45 in the lateral wall of the catheter-basic-body.

At the relatively proximal side of the opening 45 a stiffening wire 46 has been received in line with the guide wire channel 44. In the lumen 43 a thin-walled tube 47 has been received for stiffening purposes as well, as a result of which the catheter moves more easily over the guide wire. By employing the stiffening wire 46 and the support tube 47, the catheter will have also in the case of very small diameters a good buckling resistance and can be advanced properly in a longitudinal direction form the proximal end.

The basic body 50 of the catheter illustrated in the FIGS. 9 and 10 is again made up of a number of tube-like elements comprising a single lumen. In the lumen of the outer tube-like body 51 a central tube-like body 52 has been received, inside of which an inner tube-like element 53 has been received. The inner tube-like element 53 has a lumen 56 which serves as guide wire lumen. The inner tube-like body 53 has been led through the wall of the central tube-like body 42 and the wall of the outer tube-like body 51, so that an opening 57 of the guide wire channel has been formed in the wall of the basic body 50. For the purpose of sealing and mutual fixation of the different tube-like bodies, a hardened adhesive agent 58 has been arranged. The fixation can also be achieved by means of welding.

In the central tube-like body 52 a tube-like insert 54 has been arranged near the opening 57, which ensures that the lumen of the central tube-like body 52 retains an open connection to the proximal end. A stiffening wire 55 extends into the tube-like insert 54, which ensures the required buckling stiffness at the opening 57.

We claim:

1. Catheter comprising:

a tube-like basic body with a distal and a proximal ends; and at least two balloon members arranged at the distal end in series at a predetermined distance from each other;

wherein an ultrasonic probe is placed on said distal end, and is situated between each of the said balloon members; and wherein the basic body comprises at least at the distal end three coaxial tube-like bodies and wherein excitation conductors for the ultrasonic probe have been led through an interspace between two of said coaxial tube-like bodies to the proximal end.

2. Catheter as claimed in claim 1, wherein the ultrasonic probe comprises a series of piezo crystals, and at least one multiplexer which can activate the piezo crystals in a phased manner.

3. Catheter as claimed in claim 1 wherein the relatively distal balloon member is a dilatation balloon and the relatively proximal balloon member has been designed for the purpose of positioning a stent.

4. Catheter as claimed in claim 1 wherein said catheter contains a lumen designated for the purpose of guiding a guide wire and which lumen has an opening in the outer wall of said basic body at the relatively proximal end of the relatively proximal balloon member.

5. Catheter as claimed in claim 4, wherein a stiffening wire is received near the opening of the guide wire lumen in the basic body.

6. Catheter as claimed in claim 4, wherein the basic body is formed from one single tube-like body comprising a plurality of lumens, and the opening of the guide wire lumen has been formed in said basic body.

* * * * *